United States Patent [19]

Paulos et al.

[11] Patent Number: 5,071,420

[45] Date of Patent: Dec. 10, 1991

[54] ISOMETRY TESTING DEVICE

[75] Inventors: Lonnie E. Paulos; E. Paul France, both of Salt Lake City; Richard L. Ellingson, Draper, all of Utah

[73] Assignee: DePuy Du Pont Orthopaedics, Warsaw, Ind.

[21] Appl. No.: 691,379

[22] Filed: Apr. 25, 1991

[51] Int. Cl.$^5$ ............................................. A61B 17/56
[52] U.S. Cl. ...................................... 606/99; 606/102; 606/104
[58] Field of Search .......................... 606/102, 99, 104; 623/13

[56]  References Cited
U.S. PATENT DOCUMENTS

| | | |
|---|---|---|
| 4,312,337 | 1/1982 | Donohue . |
| 4,535,768 | 8/1985 | Hourahane et al. . |
| 4,632,100 | 12/1986 | Somers et al. . |
| 4,708,139 | 11/1987 | Dunbar, IV . |
| 4,772,286 | 9/1988 | Goble et al. . |
| 4,834,080 | 4/1989 | Brown . |
| 4,870,957 | 10/1989 | Goble et al. ........................ 623/13 X |
| 4,911,153 | 3/1990 | Border . |
| 4,950,271 | 8/1990 | Lewis et al. .......................... 606/102 |
| 4,969,895 | 11/1990 | McLeod et al. ................. 606/104 X |

OTHER PUBLICATIONS

"OSI Isometric ACL Reconstruction System", Orthopedic Systems, Inc., California.
L. Paulos, M.D., "Concept Precise ACL Guide System", *Surgical Technique*, pp. 71, 95, Salt Lake City, Utah.
Acufex Cruciate Reconstruction Accessories Brochure, Acufex Microsurgical, Inc., 1986.
J. L. Lewis et al., "Factors Affecting Graft Force in Surgical Reconstruction of the Anterior Cruciate Ligament", *Journal of Orthopaedic Research*, vol. 8, No. 4, pp. 514–521, 1990.
D. I. Bylski-Austrow et al., "Anterior Cruciate Ligament Replacements: A Mechanical Study of Femoral Attachment Location, Flexion Angle at Tensioning, and Initial Tension", *Journal of Orthopaedic Research*, vol. 8, No. 4, pp. 522-531, 1990.
B. Graf, M.D., "Isometric Placement of Substitutes for the Anterior Cruciate Ligament", reprinted from *The anterior Cruciate Deficient Knee*, D. W. Jackson, M.D., Editor, Mosby (Publication Pending).
"Measure Cruciate Ligament Isometry", MEDmetric Corporation, San Diego, Calif., 1988.
"Surgical Techniques", Arthrex Arthroscopy Instruments, Inc., pp. 1–38, 1991.
Purnell et al., "Arthroscopic Anterior Cruciate Ligament Reconstruction", Johnson & Johnson Orthopaedics, pp. 1-24, 1988.
T. Rosenberg, M.D., "Arthroscopic Technique for Anterior Cruciate Reconstruction", Acufex Microsurgical, Inc., 1988.

*Primary Examiner*—Robert A. Hafer
*Assistant Examiner*—Kevin G. Rooney
*Attorney, Agent, or Firm*—Barnes & Thornburg

[57] ABSTRACT

A device for determining the isometric point of a knee cruciate ligament replacement in a femur after a tibial tunnel has been prepared by attaching a screw to an estimated placement point on the femur with a strand attached to the screw and extending away therefrom. The device comprises a holder, a driver disposed in the holder to engage and drive the screw into the femur, a fitting for positioning the holder to the mouth of the tunnel on the outer anterior tibial surface, a gauge calibrated to provide a selected tension on the strand, and means for attaching the gauge to the holder. The gauge comprises an excursion scale to indicate the movement of the strand when the knee is flexed, a spring for applying a selected tension to the strand, and a gripper for the strand. The holder and the gauge are configured to hold the strand as it extends away from the screw through the tibial tunnel to the gauge, whereby, when the strand is gripped to the spring to have the selected tension thereon and the knee is flexed, the excursion of the point at which the screw is attached will be represented on the excursion scale.

15 Claims, 2 Drawing Sheets

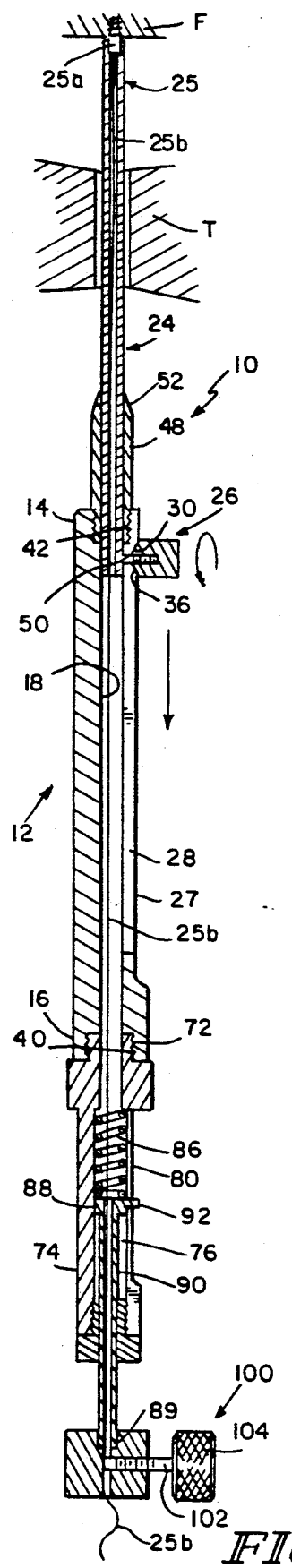
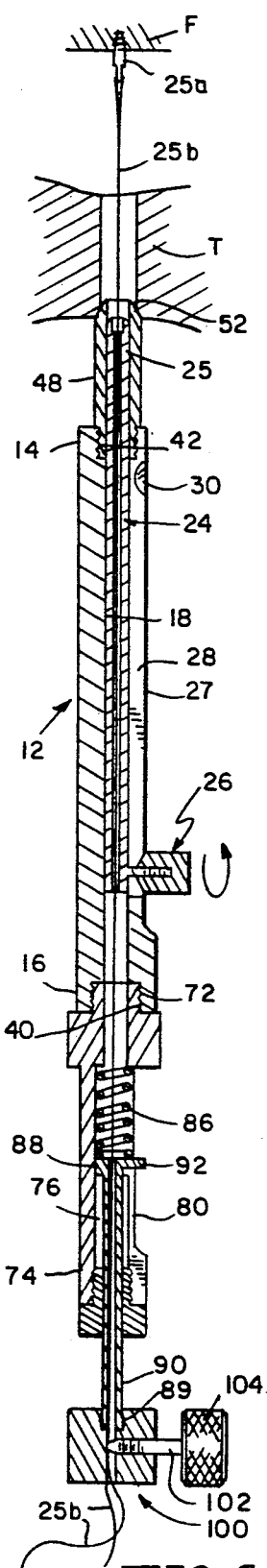
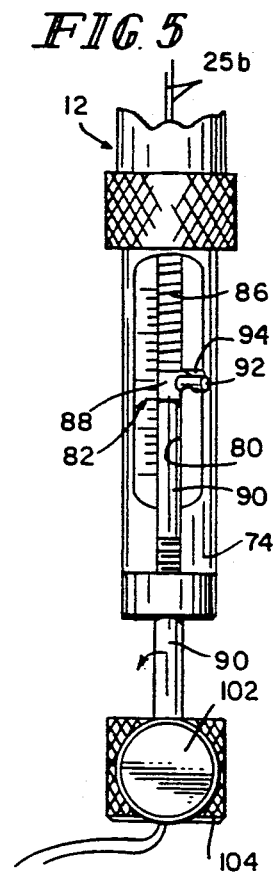
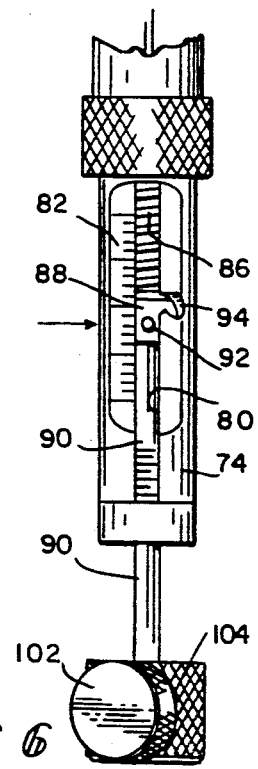
FIG.5
FIG.3
FIG.4
FIG.6

ISOMETRY TESTING DEVICE

BACKGROUND OF THE INVENTION

1. Field of the Invention

The present invention relates to isometry testing devices, and more particularly to devices for determining the isometric point of a knee cruciate ligament replacement in a femur after a tibial tunnel has been prepared by attaching a fastening means to an estimated placement point on the femur with strand means, such as a heavy suture, attached to the fastening means and extending away therefrom to be utilized with the device.

The manner in which cruciate ligaments are replaced is well known and well documented. In our copending patent application Ser. No. 07/650,680, filed Feb. 5, 1991, titled *Variable Angle, Selective Length Tibial Drill Guide*, we discussed the location and preparation of the tibial tunnel in which the tibial portion of the cruciate ligament replacement is anchored. After such a tibial tunnel is prepared, a similar tunnel for anchoring the femur portion of the cruciate replacement in the femur is prepared. The tunnel in the femur must be located carefully with respect to the tibial tunnel and surgeons have found that the femur tunnel should begin at a point which is referred to as the isometric point on the femur. This isometric point is well known and well described in the literature. Reference is made to an article by Ben Graf, M.D., University of Wisconsin, Madison, Wis., titled *Isometric Placement of Substitutes for the Anterior Cruciate Ligament*. Dr. Graf's article outlines the value of locating the isometric point and using that point to locate the femur tunnel for anchoring the femur portion of the cruciate ligament replacement. Dr. Graf's article shows how the point may be located and proposes a device for testing the isometry of any selected point, the device being shown in sectional view if FIG. 1 and in use in FIG. 2.

2. Prior Art

This article by Dr. Graf and the device and method disclosed therein are referenced in detail not only to discuss isometric placement, but to discuss the presently known prior art devices over which the present invention is a significant improvement. For instance, the device shown in Dr. Graf's article clearly is a tension application device utilizing a spring to apply the desired tension to the strand means (suture) attached to a estimated isometric point with an excursion measuring means to show the movement of the strand means when the knee is flexed. As explained by Dr. Graf, when this movement of the strand means is less than or equal to 1.5 mm, the isometric point is very close to or on the point to which the strand means is fastened. It is necessary to place the strand means under a given tension because the cruciate ligament and the replacement cruciate ligament will be under tension in the knee. This tension causes the knee to react during flexure as it would with a ligament in place.

The prior art, therefore, teaches attaching a suture or other flexible strand means to what Dr. Graf refers to as the "initial point selection" and then connecting that suture to a spring-loaded tension gauge which will read the excursion movement of the strand means when the knee is flexed. Another example of such a device is a device offered by MEDmetric Corporation which comprises a tension gauge that measures excursion. The MEDmetric device comes equipped with a plurality of tool noses which fit on the front of the device to engage it with the knee. Acufex Microsurgical, Inc. has a brochure out showing what appears to be the device disclosed in Dr. Graf's article discussed above.

Further reference is made to an article in the *Journal of Orthopedic Research* by D. I. Bylski-Austrow, et al. titled *Anterior Cruciate Ligament Replacements: A Mechanical Study of Femoral Attachment Location, Flexion Angle at Tensioning, and Initial Tension*. This reference clearly teaches the importance of precise placement of cruciate ligament replacement anchoring points.

Finally, U.S. Pat. No. 4,632,100 discloses a fastening means to which a suture is attached, but it will be appreciated that the present invention does not involve any particular type of fastening means or strand means.

In summary, therefore, it is well known that the isometric point must be carefully located and that it may be located by attaching flexible strand means to an estimated point and applying tension to that strand means while the knee is flexed to observe the excursion movement of the strand means.

The present invention is an improvement over what is known for several substantial reasons including a self-contained driver for the fastening means disposed in the device for ease of use with the device and for retraction into the device after the fastening means is attached. This feature permits only one entry to be made through the tibial tunnel to attach the fastening means and then to measure the excursion. Without the self contained, retractable driver, the surgeon would have to enter through the tunnel to fasten the devise and then to reenter the tunnel with the tension/excursion test device.

Another important feature of the present invention not shown in the prior art is the provision of a plurality of separate gauges attachable to the holder or handle portion of the device, each gauge being provided with a preselected tension capability to match the selected ligament replacement material.

Another important feature of the present invention not shown nor suggested by the prior art is that it is designed to have a first barrel portion which acts as a handle for the driver and a detachable second barrel portion which serves as the tension and excursion gauge. The importance of this feature will be more fully discussed hereinafter, but it will be understood by surgeons working in the field that such a device should be relatively small in diameter and compact to be easily held in a very confined surgical situation. It will be seen that the illustrated and preferred embodiment of the present invention is generally an elongated, cylindrically shaped instrument or tool ideally suited for use in what is referred to as arthroscopic surgery in which the surgeon works in a confined situation.

BRIEF SUMMARY OF THE INVENTION

The present invention, therefore, is a device for determining the isometric point of a knee cruciate ligament replacement in a femur after a tibial tunnel has been prepared by attaching a fastening means to an estimated placement point on the femur with strand means attached to the fastening means and extending away therefrom to be used in the device. The device comprises a holder, a driver disposed in the holder to engage and drive the fastening means into the femur, means for positioning the holder to the mouth of the tunnel on the outer interior tibial surface, a gauge calibrated to provide a selected tension on the strand means, and means for attaching the gauge to the holder. The gauge comprises means providing an excursion scale to indicate the movement of the strand means when the knee is flexed, tension means for applying a selected tension to the strand means, and means for gripping the strand means to the tension means. The holder and the gauge are configured to hold the strand means as it extends away from the fastening means through the tibial tunnel to the gauge, whereby, when the strand means is gripped to the tension means to have the selected tension thereon and the knee is flexed, the excursion of the point at which the fastening means is attached will be represented on the excursion scale.

The device is preferably provided with a plurality of such gauges provided as a kit with the holder, each gauge being provided with a preselected tension capability to match the selected ligament replacement materials. Further, each gauge comprises a cartridge configured to be aligned with the holder, the cartridge having an opening therethrough in communication with the tunnel in the tibia, the tension means comprising a spring disposed in the opening, and means for loading the spring to apply a selected tension to the strand means. The loading means preferably has a cocked position which preloads the spring and a released position which is determined by the spring and the strand means. The gripping means is configured to grip the strand means to the loading means, whereby, when the strand means is gripped tightly to the loading means when it is in the cocked position and the loading means is released from the cocked position, the spring will apply a preselected tension to the strand means.

BRIEF DESCRIPTION OF THE DRAWINGS

FIG. 3 is a transverse sectional view of the present invention with the driver fully extended for attaching the screw to the femur;

FIG. 4 is a view similar to FIG. 3 but with the driver retracted and the fitting nesting in the predrilled opening of the tibial and the distal end of the strand means secured to the device for loading;

FIG. 5 is a partial right side view of the lower end of FIG. 4 illustrating the nesting of the lug in the preload notch just prior to releasing; and FIG. 6 is a view similar to FIG. 5 but with the lug released from the notch and rotated counterclockwise to allow the lug to act as a pointer to indicate the load and excursion being exerted on the strand.

Referring to FIGS. 1, 2, 3 and 4, it will be seen that the illustrative device 10 for determining the isometric point comprises a first barrel 12 or a holder as hereinabove described having a forward end 14 and a rearward end 16 with a center passageway 18 (FIGS. 3 and 4) extending longitudinally therethrough. A driver 24 is disposed in this passageway 18 for projection from the barrel 12 as shown in FIG. 3 and for retraction rearwardly into the passageway as shown in FIG. 4. This driver 24 has a driving head 25 for holding and driving a fastening means, such as the illustrative screw 25a. The particular screw or fastening means 25a is such that it can be driven into the cortical bone of the femur F to be securely anchored at the estimated isometric point. As suggested in Dr. Graf's article discussed above, strand means such as the illustrative sutures 25b may be attached to the fastening means 25a to be used with the tension applicator and excursion measuring device of the present invention.

Figure 1:
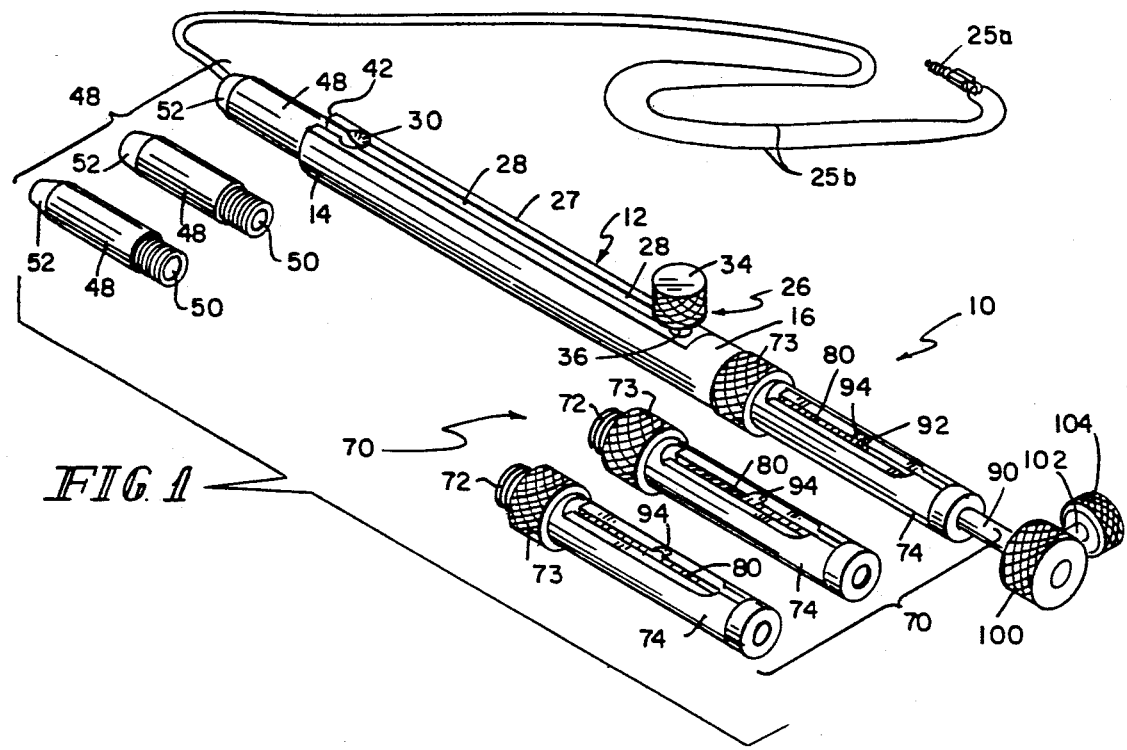
FIG. 1 is a perspective view of the present invention and shows interchangeable kit adaptors.
Figure 2:
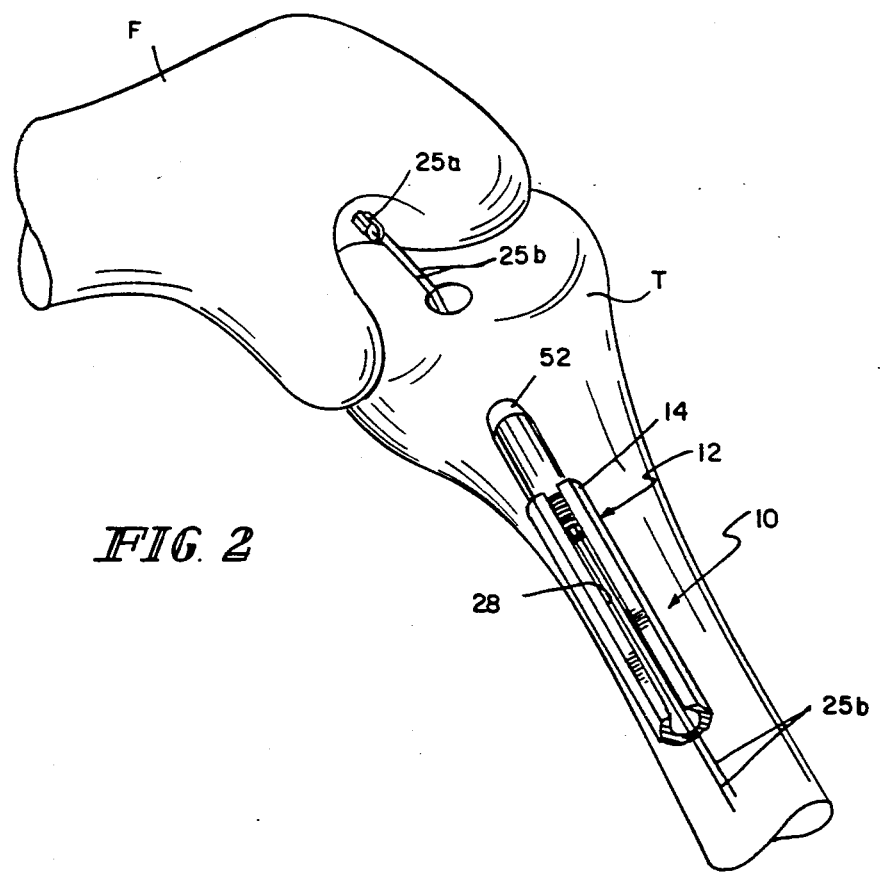
FIG. 2 is a perspective view of a portion of the present invention in its working relationship with tibial and femur elements of a knee joint.

Means 26 is provided for holding the driver 24 in its projected position for holding and driving the fastening means 25a and in its retracted position within the passageway 18 of the barrel 12. In the illustrative embodiment, the barrel 12 is formed to have a longitudinally extending flat 27 bordering a central, longitudinally extending slot 28 through which the means 26 extends. The illustrative means 26 is a threaded member rigidly attached to the driver 24. A spherical depression 30 is disposed at the forward end of the slot 28 to be the anchoring point for a knurled nut 34 having a conical or spherical engaging portion 36. When this nut 34 is threaded on the means 26 and tightened, it will hold the driver 24 in a selected position. When the nut 34 is tightly engaged into the depression 30, the driver 24 is firmly locked in position for use with the fastening means 25a. When the nut 34 is tightened against the flat 27 near the rearward end 16 of the barrel 12, the driver 24 will be in its retracted position within the barrel as seen in FIG. 4. The driver 24 is provided with a central longitudinal passageway through which the strand means 25a may extend to feed into the passageway 18 as shown in the drawings.

The illustrative barrel 12 is provided with a threaded opening 40 at the mouth of the passageway 18 at rearward end 16 and a threaded opening 42 at the mouth of passageway 18 at forward end 14. Means such as the illustrated fitting 48 may be threadedly engaged into the opening 42 for positioning the device 10 in the correct position at the mouth of the tibial tunnel as shown in FIG. 1. This illustrative fitting 48 has a center passage 50 through which the driver 24 moves as shown in the drawings. Also, illustratively, a plurality of fittings 48 may be provided for tunnels having larger or smaller mouth openings. It has been found that it is better to have the device properly engage the mouth of the tibial T tunnel.

Device 10 of the present invention further comprises a plurality of gauges 70 to be attached to the barrel 12, each gauge having a selected tension capability as described hereinabove. For example, five gauges 70 having 5, 15, 30, 40 and 50 pound tension capability may be provided for the surgeon to select a tension to match the nature of the replacement ligament. The illustrative gauge 70 is provided with threaded fastening means 72 for quickly engaging the opening 40 in the barrel 12. The knurled cripping portion 73 is provided to accommodate this threaded attachment. The illustrative gauge 70 comprises a second barrel or cartridge 74 having a central, longitudinally extending opening 76 (FIGS. 3 and 4) extending therethrough. A longitudinal slot 80 is provided with indicia means 82 engraved therealong on flat surface bordering the slot as illustrated. It will be appreciated that this means 82 may be graduated in millimeters to show excursion.

A compression spring 86 is disposed in the central opening 76 to provide the tension means of the present invention. A plunger 88 having a rearwardly extending stem portion 90 is disposed in the central opening 76 to be driven rearwardly by the spring 86. A lug 92 carried by this plunger may be engaged into a transversely extending notch 94 to preload the spring 86 (FIG. 5) so that the energy in the spring can be released against the strand means 25b as described hereinafter. Specifically, the lug 92 and the notch 94 are means for cocking the gauge 70 or preloading the spring 86.

The stem 90 has a threaded rearward end portion 89 on which is mounted a strand means 25b gripper 100 which has an illustrative threaded engaging member 102 and a knurled knob 104.

By having a plurality of gauges 70 as shown in FIG. 1, each one of which is preselected to provide a desired tension on the strand means 25b, the surgeon can select quickly and easily a tension which will match the characteristics of the replacement cruciate ligament and thereafter not have to worry about any further adjustment during the procedure using the device. It will be perceived that each gauge 70 may be rather small and convenient to use in connection with the streamlined barrel 12 and driver 24.

With the device 10 of the present invention, the excursion of any selected isometric point can be easily checked with only one entry through the tibial T tunnel per selected point. Specifically, with the tibial tunnel already prepared, a fastening means 25a may be attached to the driver 24 with the strand means 25b extending rearwardly through the barrel 12 and gauge 70 to be loosely extending through the gripper 100. It will be appreciated that the fastening means 25a may be held securely attached to the driver 24 by holding slight tension on the strand means 25b. The driver in its projected position may then be inserted upwardly through the tibial T tunnel to place the fastening means at what is estimated to be the appropriate isometric point, and the barrel may be twisted to drive the fastening means into that point on the femur. Without removing the device 10 from the engagement with the tunnel (the fitting 48 with its nose 52 against the mouth of the tunnel), the driver 24 may be retracted into the passageway 18 to be out of the knee joint so that the knee can be flexed. After the driver 24 is so retracted, the surgeon may pull rearwardly on the strand means 25 to apply a reasonably small tension, basically to take up the slack with the spring 86 preloaded. At that point, the strand means may be gripped to the stem 90 of the plunger 88 which has its lug 92 in the notch 94. At that point, the surgeon may rotate the stem 90 to release the lug 92 from the notch 94 to have the spring 86 apply its compression load to the strand means 25, i.e., to apply a preselected tension to the strand means 25b. Then, the knee can be flexed through its desired range of movement as taught by Dr. Graf in his above referenced article to watch the excursion of the lug 92 adjacent the excursion scale 82. If the excursion of the plunger 88 to which the strand means 25b is attached is less than 1.5 mm, it is believed that the fastening means 25a is attached to the desired isometric point. That point, therefore, may be used to locate the anchoring tunnel in the femur.

What is claimed is:

1. A device for determining the isometric point of a knee cruciate ligament replacement in a femur after a tibial tunnel has been prepared by attaching a fastening means to an estimated placement point on the femur with strand means attached to the fastening means and extending away therefrom, said device comprising an elongated first barrel having a forward end, a rearward end, and a longitudinally extending center passage, a driver disposed in said center passage for projection and retraction through said forward end of said first barrel to engage and drive the fastening means into the femur, means for locking said driver in a projected position to engage the fastening means and a retracted position in said first barrel, means for positioning said forward end of said first barrel to the mouth of the tunnel on the outer anterior tibial surface, a gauge calibrated to provide a selected tension on the strand means, and means for attaching said gauge to the rearward end of said first barrel, said gauge comprising means providing an excursion scale to indicate the movement of said strand means when the knee is flexed, tension means for applying a selected tension to the strand means, and means for gripping the strand means to said tension means, said barrel and said gauge being configured to hold the strand means as it extends away from the fastening means through the tibial tunnel into said first barrel to said gauge, whereby, when the strand means is gripped to said tension means to have the selected tension thereon and the knee is flexed, the excursion of the point at which the fastening means is attached will be represented on said excursion scale.

2. The device of claim 1 including a plurality of said gauges provided as a kit with said first barrel, each said gauge provided with a preselected tension capability to match the selected ligament replacement materials.

3. The device of claim 1 in which said gauge comprises a second barrel configured to be aligned with the first barrel at said rearward end, said second barrel having a central longitudinal opening therethrough in communication with said center passage, said tension means comprising a spring disposed in said opening, and means for loading said spring to apply a selected tension to the strand means, said loading means having a cocked position which preloads said spring and a released position which is determined by said spring and the strand means, and said gripping means being configured to grip the strand means to said loading means, whereby, when the strand means is gripped tightly to said loading means when it is in said cocked position and said loading means is released from said cocked position, said spring will apply a preselected tension to the strand means.

4. The device of claim 3 in which said spring is a compression spring disposed in the forward end of said central opening of said second barrel, said loading means being a plunger disposed for reciprocation in said central opening toward and away from said first barrel in driving engagement with said spring.

5. The device of claim 4 in which said excursion scale comprises indicia means providing a scale spaced along said second barrel and a pointer carried by said plunger adjacent said scale.

6. The device of claim 5 in which said plunger has a block portion engaged with said spring and a stem portion extending rearwardly from said central opening of said second barrel, said stem portion having a rearward portion extending rearwardly out of said second barrel, said gripping means being carried by said rearward portion of said stem portion.

7. The device of claim 6 in which said means for positioning said forward end of said first barrel comprises a fitting having a central passageway through which said driver moves, means for removably attaching said fitting to said forward end of said first barrel.

8. The device of claim 6 including a plurality of said gauges provided as a kit with said first barrel, each said gauge provided with a selected tension capability to match the selected ligament replacement material.

9. The device of claim 7 including a plurality of said fittings provided as a kit with said first barrel, each said fitting being sized and shaped to fit a tunnel of a specific size.

10. A device for determining the isometric point of a knee cruciate ligament replacement in a femur after a tibial tunnel has been prepared by attaching a fastening means to an estimated placement point on the femur with strand means attached to the fastening means and extending away therefrom, said device comprising a holder having a forward end, a rearward end, and a passage extending from end to end, a driver disposed in said passage for projection and retraction through said forward end to engage and drive the fastening means into the femur, means for locking said driver in a projected position to engage the fastening means and a retracted position in said holder, means for positioning said forward end to the mouth of the tunnel on the outer anterior tibial surface, a gauge calibrated to provide a selected tension on the strand means, and means for attaching said gauge to the rearward end of said holder, said gauge comprising means providing an excursion scale to indicate the movement of said strand means when the knee is flexed, tension means for applying a selected tension to the strand means, and means for gripping the strand means to said tension means, said holder and said gauge being configured to hold the strand means as it extends away from the fastening means through the tibial tunnel into said holder to said gauge, whereby, when the strand means is gripped to said tension means to have the selected tension thereon and the knee is flexed, the excursion of the point at which the fastening means is attached will be represented on said excursion scale.

11. The device of claim 10 in which said gauge further comprises a spring cartridge configured to be aligned with the holder at said rearward end, said cartridge having a central opening therethrough in communication with passage of said holder, said tension means comprising a spring disposed in said opening, and means for loading said spring to apply a selected tension to the strand means, said loading means having a cocked position which preloads said spring and a released position which is determined by said spring and the strand means, and said gripping means being configured to grip the strand means to said loading means, whereby, when the strand means is gripped tightly to said loading means when it is in said cocked position and said loading means is released from said cocked position, said spring will apply a preselected tension to the strand means.

12. A device for determining the isometric point of a knee cruciate ligament replacement in a femur after a tibial tunnel has been prepared by attaching a fastening means to an estimated placement point on the femur with strand means attached to the fastening means and extending away therefrom, said device comprising a holder, a driver disposed in said holder to engage and drive the fastening means into the femur, means for positioning said holder to the mouth of the tunnel on the outer anterior tibial surface, a gauge calibrated to provide a selected tension on the strand means, and means for attaching said gauge to said holder, said gauge comprising means providing an excursion scale to indicate the movement of said strand means when the knee is flexed, tension means for applying a selected tension to the strand means, and means for gripping the strand means to said tension means, said holder and said gauge being configured to hold the strand means as it extends away from the fastening means through the tibial tunnel to said gauge, whereby, when the strand means is gripped to said tension means to have the selected tension thereon and the knee is flexed, the excursion of the point at which the fastening means is attached will be represented on said excursion scale.

13. The device of claim 12 including a plurality of said gauges provided as a kit with said holder, each said gauge provided with a preselected tension capability to match the selected ligament replacement materials.

14. The device of claim 12 in which said gauge comprises a cartridge configured to be aligned with said holder, said cartridge having an opening therethrough in communication with the tunnel in the tibia, said tension means comprising a spring disposed in said opening, and means for loading said spring to apply a selected tension to the strand means, said loading means having a cocked position which preloads said spring and a released position which is determined by said spring and the strand means, and said gripping means being configured to grip the strand means to said loading means, whereby, when the strand means is gripped tightly to said loading means when it is in said cocked position and said loading means is released from said cocked position, said spring will apply a preselected tension to the strand means.

15. The device of claim 14 in which said means for attaching said gauge to said holder is a detachable means, and in which a plurality of gauges is provided as a kit with said holder, each said gauge provided with a preselected tension capability to match the selected ligament replacement materials.

* * * * *